US00PP33053P2

(12) United States Plant Patent
Ammerlaan

(10) Patent No.: US PP33,053 P2
(45) Date of Patent: May 11, 2021

(54) ***ECHEVERIA* PLANT NAMED 'OVPEARLS05'**

(50) Latin Name: *Echeveria pulidonis*
Varietal Denomination: OVPEARLS05

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/899,822

(22) Filed: Jun. 12, 2020

(30) Foreign Application Priority Data

Nov. 27, 2019 (QZ) ..... PBR 2019/3110

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct variety of *Echeveria* plant named 'OVPEARLS05' which is characterized by an abundance of dark greyed-green and heavily glaucescent foliage which is tightly held in a basal rosette, foliage which is conspicuously margined greyed-purple along the distal margins and apex and heavily suffused with greyed-purple at and towards the apex of the abaxial foliar surface. The new variety has shown to be uniform and stable in the resulting generations from asexual propagation.

4 Drawing Sheets

Latin name of the genus and species: The Latin name of the genus and species of the novel variety disclosed herein is *Echeveria pulidonis*.

Variety denomination: The inventive variety of *Echeveria* disclosed herein has been given the variety denomination 'OVPEARLS05'.

CROSS REFERENCE TO RELATED APPLICATIONS

This application claims priority to the Community Plant Variety Rights application number 2019/3110, filed on Nov. 27, 2019, which is herein incorporated by reference.

BACKGROUND OF THE INVENTION

Parentage: 'OVPEARLS05' is a naturally-occurring, whole-plant mutation of an unnamed *Echeveria pulidonis* plant (not patented) which was discovered by the inventor in March of 2009 at a commercial greenhouse in Bleiswijk, the Netherlands. The mutation was noted for its abundance of dark greyed-green, glaucous foliage with conspicuous dark red margins.

Asexual Reproduction: Asexual reproduction of the new cultivar 'OVPEARLS05', by way of rooting leaf cuttings, was first initiated in March of 2009 at the inventor's commercial greenhouse in Bleiswijk, the Netherlands. Through eight subsequent generations, the unique features of this cultivar have proven to be stable and true to type.

SUMMARY OF THE INVENTION

The cultivar 'OVPEARLS05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS05'. These characteristics in combination distinguish 'OVPEARLS05' as a new and distinct *Echeveria* cultivar:

1. 'OVPEARLS05' exhibits a globular plant form with an abundance of foliage tightly held in a basal rosette; and
2. 'OVPEARLS05' exhibits dark greyed-green, heavily glaucescent foliage; and
3. 'OVPEARLS05' exhibits foliage which is conspicuously margined greyed-purple, generally appearing as a dark red coloration along the distal margins and apex; and
4. 'OVPEARLS05' exhibits heavy suffusion of greyed-purple at and towards the apex of the abaxial foliar surface.

BOTANICAL DESCRIPTION OF THE PLANT

Figure 1:
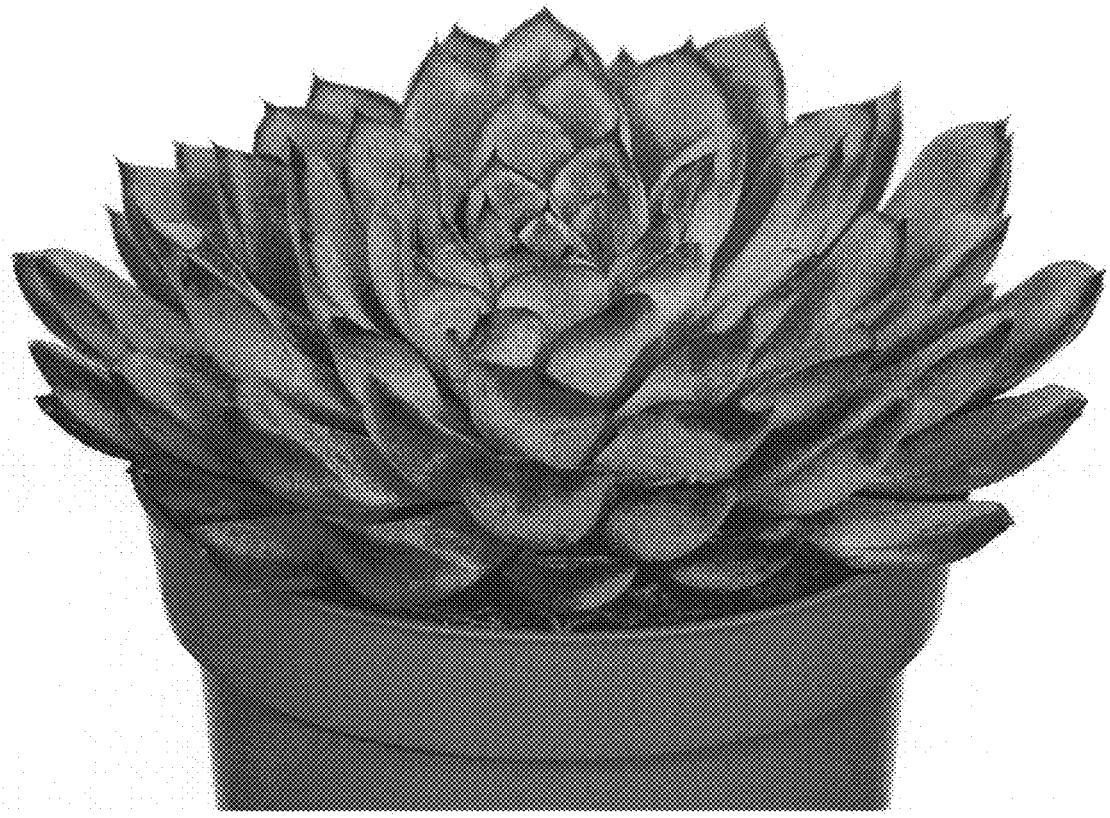
FIG. 1 illustrates, as nearly true as it is reasonably possible to make the same in color photographs of this type, an exemplary plant of 'OVPEARLS05' grown in a commercial greenhouse in Bleiswijk, the Netherlands. This plant is approximately 1 year old, shown planted in a 12 cm container.
Figure 2:
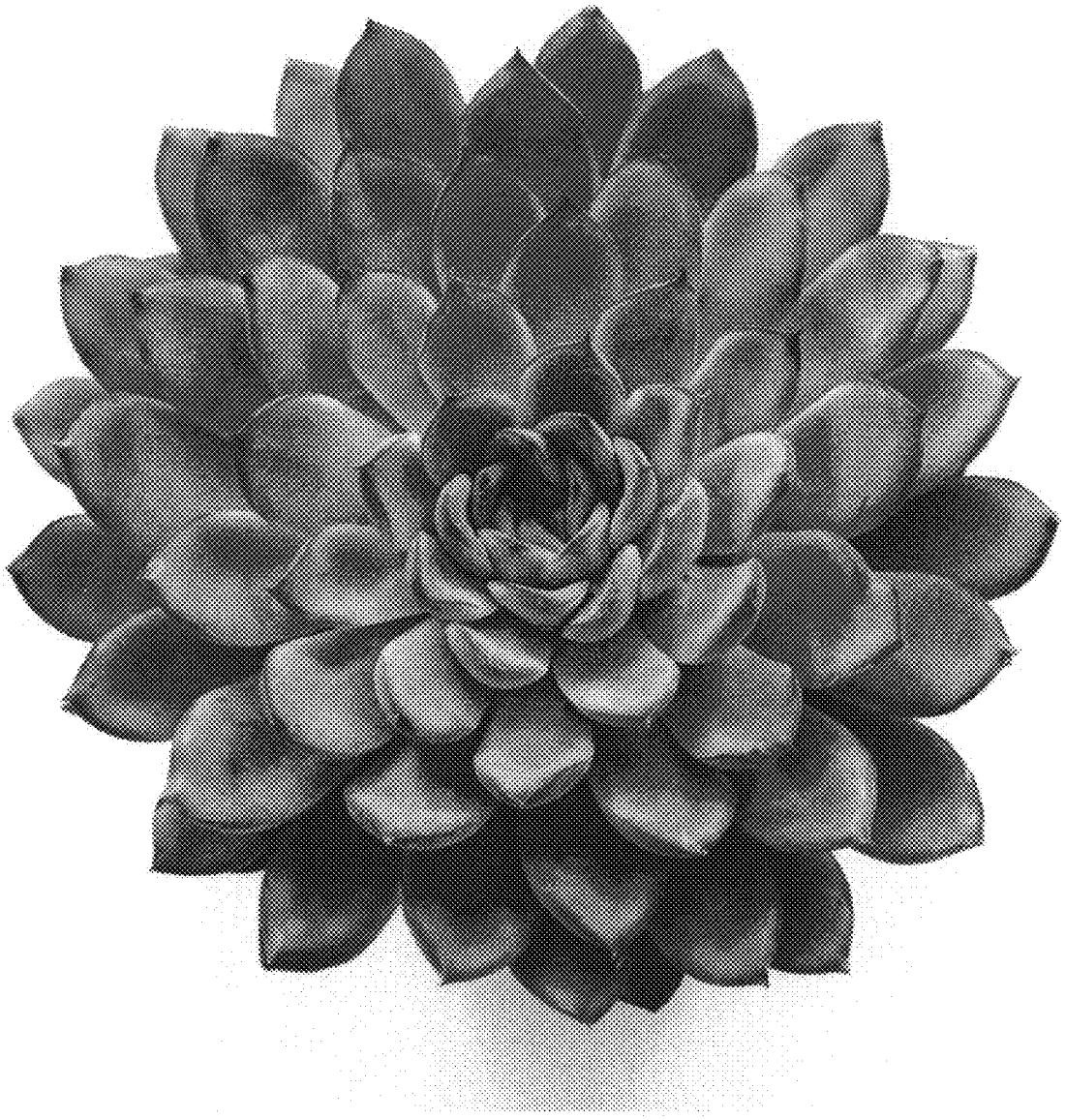
FIG. 2 illustrates, as nearly true as it is reasonably possible to make the same in color photographs of this type, the typical foliage arrangement of 'OVPEARLS05'.
Figure 3:
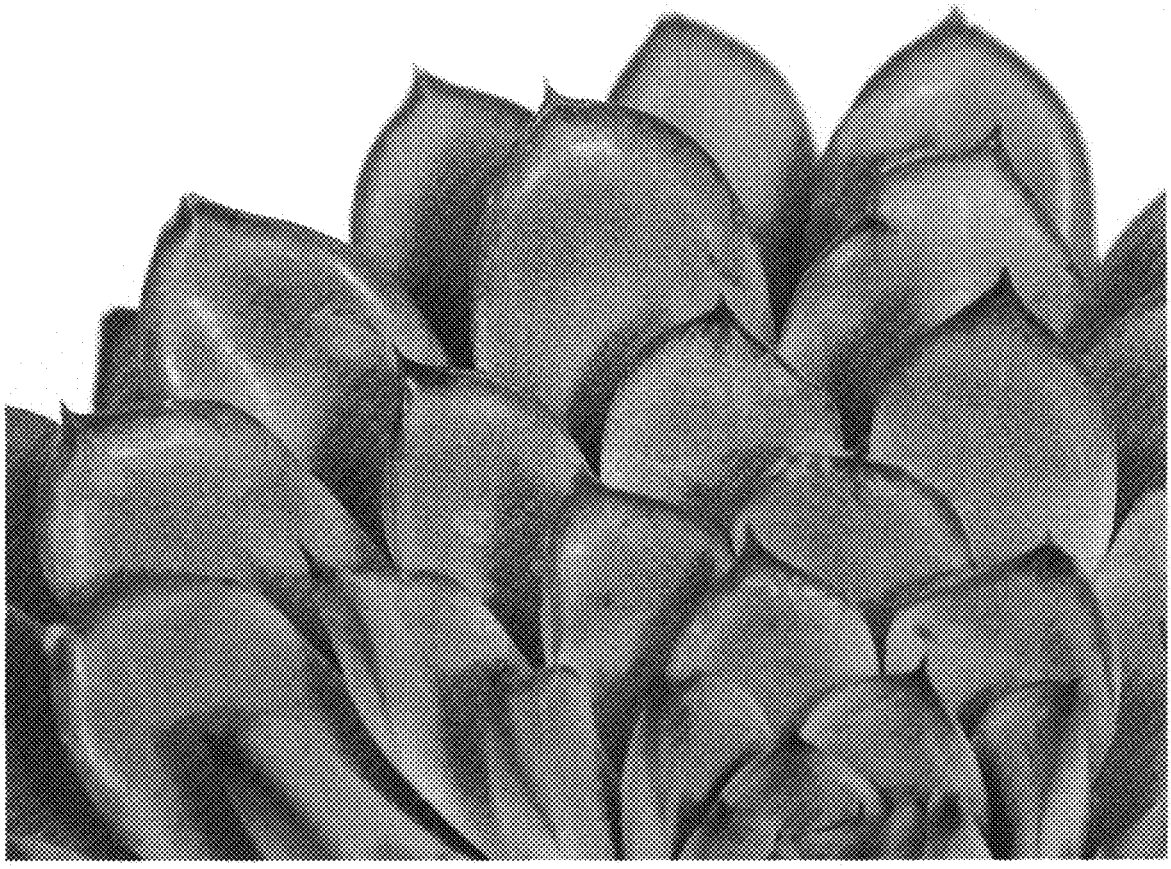
FIG. 3 illustrates, as nearly true as it is reasonably possible to make the same in color photographs of this type, the adaxial surface of the mature foliage 'OVPEARLS05'.
Figure 4:
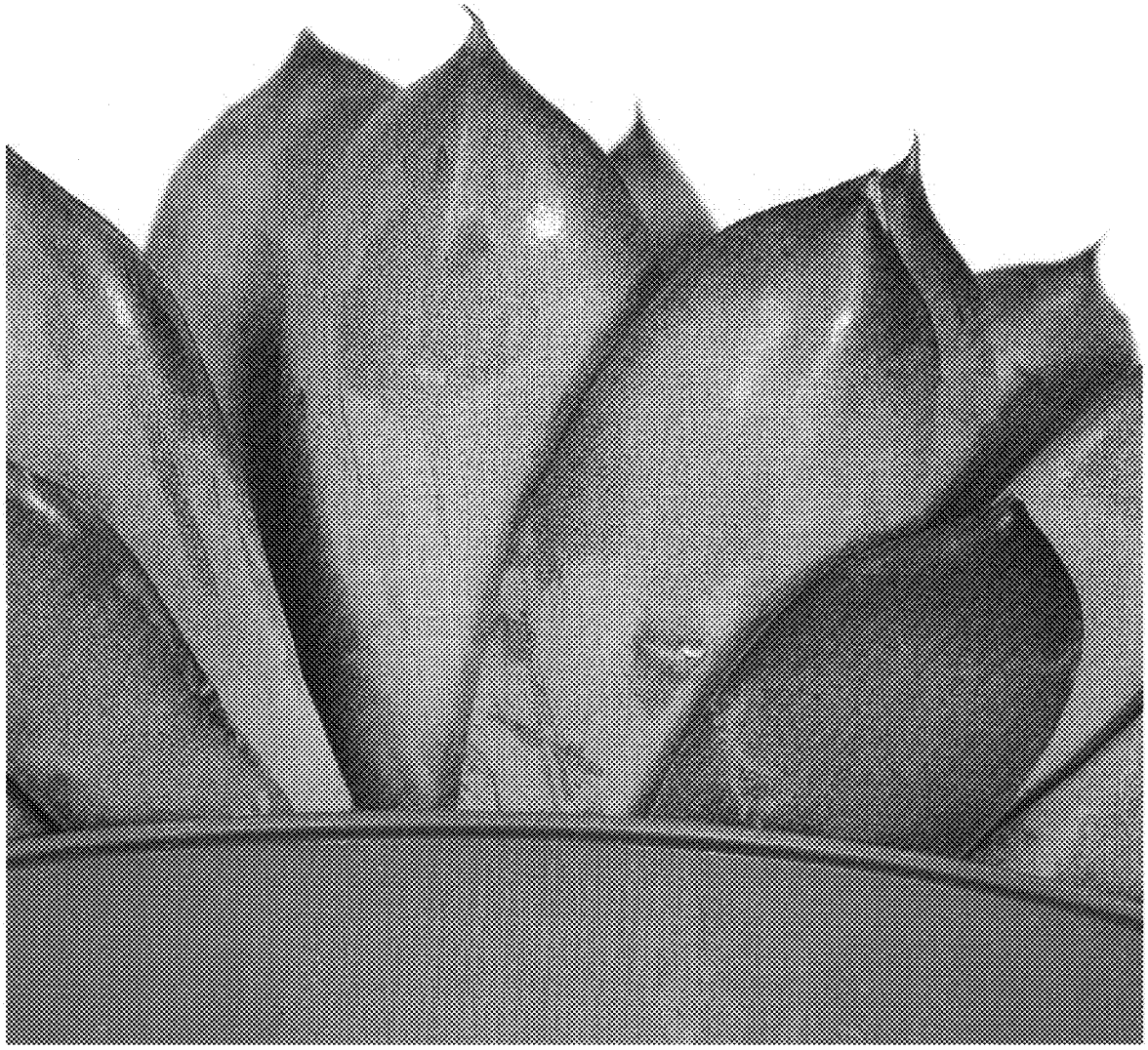
FIG. 4 illustrates, as nearly true as it is reasonably possible to make the same in color photographs of this type, the abaxial surface of the mature foliage 'OVPEARLS05'.

The following observations and measurements made in November of 2019 describe averages from a sample set of six specimens of 1 year old 'OVPEARLS05' plants grown in 12 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS05' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'OVPEARLS05' and a comparison with the parent and closest known comparator is provided below.

Plant description:

*Growth habit*.—Succulent perennial with foliage growing in a compact, non-branched basal rosette.

*Plant form*.—Globular.

*Height from soil level to top of foliar plane*.—5.0 cm.

*Plant spread*.—Average of 15.7 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 92 leaves per rosette.

*Shape*.—Narrow obovate to broad oblanceolate.

*Dimensions*.—7.4 cm long, 2.1 cm wide, and 0.75 cm thick, on average.

*Aspect*.—Very slightly concave; distal portion of the leaf is curled upward at an approximate angle of 40 degrees to the proximal portion of the leaf.

*Attitude*.—Foliage is held upright and outward at and near the center of the rosette and becomes progressively more relaxed towards the outer whorls of foliage.

*Apex*.—Abruptly acute.

*Base*.—Long cuneate.

*Margin*.—Entire; not undulated.

*Pubescence, texture and luster of the adaxial surface*.—Glabrous, smooth, and strongly glaucescent.

*Pubescence, texture and luster of the abaxial surface*.—Glabrous, smooth, and strongly glaucescent.

*Color*.—Juvenile foliage, adaxial surface — Greyed-green, nearest to RHS 191A, and fading to yellow-green towards the base, nearest to RHS 145C; margined greyed-green, nearest to RHS 193D, and becoming margined with greyed-purple towards and at the apex, nearest to RHS 183B. Leaves are covered with a thin layer of epicuticular wax which is colored greyed-green, nearest to in between RHS 188A and 188B. Juvenile foliage, abaxial surface — Greyed-green, nearest to RHS 191B, and fading lighter towards the base, nearest to RHS 193B; margined greyed-green, nearest to in between RHS 193C and 193D, and becoming margined with greyed-purple towards and at the apex, nearest to RHS 183B. Leaves are covered with a thin layer of epicuticular wax which is colored greyed-green, nearest to RHS 188C. Mature foliage, adaxial surface — Greyed-green, nearest to RHS 191A, and fading to yellow-green towards the base, nearest to RHS 147D; margined greyed-green, nearest to in between RHS 192A and 192B, and becoming margined with greyed-purple towards and at the apex, nearest to RHS N186C. Leaves are covered with a thin layer of epicuticular wax which is colored greyed-green, nearest to in between RHS 188A and 188B. Mature foliage, abaxial surface — Greyed-green, nearest to RHS 194A, fading to yellow-green towards the base, nearest to RHS 147D, and becoming heavily suffused with greyed-purple towards the apex, nearest to in between RHS 183A and N186C; margined greyed-green, nearest to in between RHS 193C and 193D, and becoming margined with greyed-purple towards and at the apex, nearest to RHS 186C. Leaves are covered with a thin layer of epicuticular wax which is colored greyed-green, nearest to RHS 188C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

Comparisons With the Parent Plant

Plants of the new cultivar 'OVPEARLS05' differ from the parent, an unnamed *Echeveria pulidonis* plant (not patented) in the following characteristics described in Table 1 below.

TABLE 1

| Characteristic | 'OVPEARLS05' | The parent. |
|---|---|---|
| General coloration of the mature foliage. | Greyed-green. | Yellow-green. |
| Distal portion of the leaf margins. | Conspicuously margined greyed-purple, generally appearing red. | Less conspicuously margined red. |
| Color suffusion of the abaxial surface of the mature foliage. | Suffused with greyed-purple towards and at the apex. | Not suffused with greyed-purple. |

Comparisons With the Closest Known Comparator

Plants of the new cultivar 'OVPEARLS05' differ from *Echeveria pulidonis* 'AMIECH1602' (U.S. Plant Pat. No. 29,757), which is the closest known comparator, in the following characteristics described in Table 2 below.

TABLE 2

| Characteristic | 'OVPEARLS05' | 'AMIECH1602' |
|---|---|---|
| Abundance of foliage | More abundant than AMIECH1602'. | Less abundant than 'OVPEARLS05' |
| Foliage width. | Foliage is narrower than AMIECH1602' | Foliage is wider than 'OVPEARLS05'. |
| Foliage glaucosity. | More strongly glaucescent by comparison to AMIECH1602'. | Less glaucescent by comparison to 'OVPEARLS05'. |
| General coloration of the mature foliage. | A darker shade of greyed-green by comparison to AMIECH1602'. | A lighter shade of greyed-green by comparison to 'OVPEARLS05'. |
| Distal portion of the leaf margins. | Conspicuously margined greyed-purple, generally appearing dark red. | Margined lighter greyed-purple to greyed-red, generally appearing as pink. |
| Color suffusion of the abaxial surface of the mature foliage. | Heavily suffused with greyed-purple towards and at the apex. | Not suffused with greyed-purple. |

That which is claimed is:

1. A new and distinct variety of *Echeveria* plant named 'OVPEARLS05', substantially as described and illustrated herein.

* * * * *